US007381707B2

(12) United States Patent  (10) Patent No.: US 7,381,707 B2
Lin et al.                  (45) Date of Patent:     Jun. 3, 2008

(54) TREATMENT OF DRY EYE

(75) Inventors: Connie Baozhen Lin, Belle Mead, NJ (US); Miri Seiberg, Princeton, NJ (US); Nannan Chen, Monmouth Junction, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 74 days.

(21) Appl. No.: 11/171,785

(22) Filed: Jun. 30, 2005

(65) Prior Publication Data

US 2007/0004640 A1    Jan. 4, 2007

(51) Int. Cl.
    C07K 5/10    (2006.01)
(52) U.S. Cl. .......................................... 514/18; 530/330
(58) Field of Classification Search ................ 530/330; 514/18
    See application file for complete search history.

(56) References Cited

U.S. PATENT DOCUMENTS

| | | | |
|---|---|---|---|
| 3,755,560 | A | 8/1973 | Dickert et al. |
| 4,254,105 | A | 3/1981 | Fukuda |
| 4,421,769 | A | 12/1983 | Dixon et al. |
| 4,453,941 | A | 6/1984 | Jacobs |
| 4,960,764 | A | 10/1990 | Figueroa, Jr. et al. |
| 5,216,116 | A | 6/1993 | Pawelek et al. |
| 5,218,079 | A | 6/1993 | Pawelek et al. |
| 5,225,435 | A | 7/1993 | Pawelek et al. |
| 5,227,459 | A | 7/1993 | Pawelek et al. |
| 5,260,065 | A | 11/1993 | Mathur et al. |
| 5,384,116 | A | 1/1995 | Pawelek et al. |
| 5,618,519 | A | 4/1997 | Pawelek et al. |
| 5,658,592 | A | 8/1997 | Tanihara et al. |
| 5,698,184 | A | 12/1997 | Pickart |
| 5,744,125 | A | 4/1998 | Pawelek et al. |
| 5,763,575 | A | 6/1998 | Sundelin et al. |
| 5,817,726 | A | 10/1998 | Nakada et al. |
| 5,905,125 | A | 5/1999 | Tsujimoto et al. |
| 5,942,558 | A | 8/1999 | Korb |
| 6,027,745 | A | 2/2000 | Nakada et al. |
| 6,620,419 | B1 | 9/2003 | Lintner |
| 6,797,697 | B2 | 9/2004 | Seiberg et al. |
| 2002/0197281 | A1 | 12/2002 | Seiberg et al. |
| 2003/0138388 | A1 | 7/2003 | Seiberg et al. |
| 2003/0203849 | A1 | 10/2003 | Araki et al. |
| 2005/0025810 | A1 | 2/2005 | Peyman |

FOREIGN PATENT DOCUMENTS

| | | |
|---|---|---|
| EP | 0273202 B1 | 6/1988 |
| EP | 0781 777 A1 | 12/1996 |
| JP | 1124010 A | 6/1997 |
| JP | 11197234 A | 1/1998 |
| JP | 2000136124 A | 5/2000 |
| WO | WO 96/31194 | 10/1996 |
| WO | WO 99/37279 | 7/1999 |
| WO | WO 00/62743 | 10/2000 |

OTHER PUBLICATIONS

Nishikawa (J Pharm Exp Ther. 312(1), 324-331, 2004.*

Uehara A. et al., Neutrophil Serine Proteinases Activate Human Nonepithelial Cells to Produce Inflammatory Cytoines Through Protease-Activated Receptor $2^1$, The Journal of Immunology, vol. 170, (2003)pp. 5690-5696.

Miklos Bodanszky, In Search of new methods in peptide synthesis, (1985) 449-474, International J. Peptide Protein Research 25, Munksgaard International Pubblishers Ltd. Copenhagen Denmark.

M. Seiberg, C. Paine, E. Sharlow, P. Andrade-Gordon, M. Costanzo, M. Eisinger, S. S. Shapiro, The Protease-Activated Receptor 2 Regulates Pigmentation via Keratinocyte-Melanocyte Interactions, (2000), Experimental Cell Research, 25-32, Academic Press.

E.R. Sharlow, C.S. Paine, L. Babiarz, M. Eisinger, S. Shapiro, M. Seiberg, The protease-activated receptor-2 upregulates keratinocyte phagocytosis, (2000)Journal of Cell Science 113:3093-3101, The Company of Biologists Limited.

Miri Seiberg, Christine Paine, Elizabeth Sharlow, Patricia Andrade-Gordon, Michael Constanzo, Magdalena Eisinger and Stanley S. Shapiro, Inhibition of Melanosome Transfer Results in Skin Lightening, (2000), The Journal of Investigative Dermatology, vol. 115, No. 2:162-167, The Society of Investigative Dermatology, Inc.

Chemical Abstracts vol. 127, No. 16, 1997, Colombus, Ohio, abstract No. 218497e, S. Tajima et al.Moduclation by elastin peptide VGVAPG of cell proliferation and elastin expression in human skin fibroblasts, XP002231281.

Abstract of FR2691465 issued Nov. 26, 1992 (Fabre Medicament P.).

Abstract of WO00/15188A published Mar. 23, 2000 (Sederma).

Steinhoff, et al., Proteinase-Activated Receptor-2 Mediates Itch: A Novel Pathway for Pruritus in Human Skin, The Journal of Neuroscience, Jul. 16, 2003, pp. 6176-6180.

Seeliger, S., Proinflammatory role of proteinase-activated receptor-2 in humans and mice during cutaneous inflammation in vivo, The FASEB Journal, vol. 17, Oct. 2003, pp. 1871-1885.

Lang et al., Human Corneal Epithelial Cells Express Functional PAR-1 and PAR-2, Investigative Ophthalmology & Visual Science, Jan. 2003, vol. 44, No. 1, pp. 99-105.

Gipson, Ilene K., Disribution of mucins at the ocular surface, Experimental Eye Research 78 (2004)pp. 379-388.

Nishikawa, H. et al., Protease-Activated Recpetor-2 (PAR-2)-Related Peptides Induce Tear Secretion in Rats: Involvement of PAR-2 and Non-PAR-2 Mechanisms, The Journal of Pharmacology and Experimental Therapeutics, vol. 312, No. 1, pp. 324-331.

Molino, M. et al., Interactions of Mast Cell Tryptase with Thrombin Receptors and PAR-2, The Journal of Biological Chemistry, vol. 272, No. 7, Issue of Feb. 14, 1997, pp. 4.43-4.49.

(Continued)

Primary Examiner—David Lukton

(57) ABSTRACT

The present invention relates to methods to treat dry eye in a mammal by intraocularly administering a composition comprising a peptide.

19 Claims, No Drawings

OTHER PUBLICATIONS

Nystedt, S. et al., Molecular cloning and functional expression of the gene encoding the human proteinase-activated receptor 2, Eur. J. Biochem, vol. 232, (1995) pp. 84-89.

Bohm, S. et al., Molecular cloning, expression and potential functions of the human proteinase-activated receptor-2, J. Biochem, vol. 314 (1996), pp. 1009-1016.

Bodanszky, M., In Search of new methods in peptide synthesis, Int. J. peptide Protein Res., vol. 25, (1985) pp. 449-474.

John A. Wenninger, G.N. McEwen, Jr.,International Cosmetic Ingredient Dictionary and Handbook, (1997), 1612-1613, 1626, 1654-1661,1673-1686, 1693-1697,Seventh Edition 1997, vol. 2, The Cosmetic, Toiletry, and Fragrance Association, Washington, DC.

Michael Mezei, Vijeyalakshmi Gulasekharam, Liposomes-A selective drug delivery system for the topical route of administration: gel dosage form, (1982) Journal Pharm. Pharacol. 34:473-474.

Susan M. Niemiec, Chandrasekharan Ramachandran, Norman Weiner, Influence of Nonionic Liposomal Composition on Topical Delivery of Peptide Drugs into Pilosebaceous Units: An in Vivo Study Using the Hamster Ear Model, (1995), Pharmaceutical Research, vol. 12, No. 8:1184-1188, Plenum Publishing Corporation.

Petra Boukamp, Rule T. Petrussevska, Dirk Breitkreutz, Jurgen Hornung, Alex Markham, Norbert E. Fusenig, Normal Keratinization in a Spontaneously Immortalized Aneuploid Human Keratinocyte Cell Line, (1988), The Journal of Cell Biology, vol. 106:761-771, The Rockefeller University Press.

Dezna C. Sheehan, Barbara B. Hrapchak, Theory and practice of Histotechnology, (1980), 223,224,277 Second Edition, Battle Press.

D.D. Breimer, P. Speiser, Liposomes as a Skin Drug Delivery System, Topics in Pharmaceutical Sciences (1985), Elsevier Science Publishers, New York, pp. 345-358.

McCutcheon's Emulsifiers & Detergents, 1986 North American Edition, pp. 317-324.

Cosmetics Science and Technology, 1972 John Wiley & Sons, Inc. Canada, pp. 32-43, 72-73, 443-465.

* cited by examiner

SEQUENCE LISTING

<160> NUMBER OF SEQ ID NOS: 18

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C-terminal Amidation

<400> SEQUENCE: 1

Leu Ile Gly Arg
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C-terminal amidation

<400> SEQUENCE: 2

Leu Ile Gly Lys
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 3

Leu Ile Gly Arg
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 4

Leu Ile Gly Lys
1

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C-terminal amidation
<220> FEATURE:
<221> NAME/KEY: MISC_FEATURE
<223> OTHER INFORMATION: N-terminus Palmitoyl

<400> SEQUENCE: 5

Leu Ile Gly Arg

```
<210> SEQ ID NO 6
<211> LENGTH: 4
<212> TYPE: PRT
<213> ORGANISM: Artificial Sequence
<220> FEATURE:
<223> OTHER INFORMATION: Sythetic Peptide
<220> FEATURE:
<221> NAME/KEY: MISC_FEATURE
<223> OTHER INFORMATION: N-terminus Palmitoyl
<220> FEATURE:
<221> NAME/KEY: MISC_FEATURE
<223> OTHER INFORMATION: C-terminus amidation

<400> SEQUENCE: 6

Leu Ile Gly Lys
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C-terminus palmitoyl

<400> SEQUENCE: 7

Leu Ile Gly Arg
1

<210> SEQ ID NO 8
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: N-terminus palmitoyl

<400> SEQUENCE: 8

Leu Ile Gly Lys
1

<210> SEQ ID NO 9
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C-terminus amidation
<220> FEATURE:
<221> NAME/KEY: MISC_FEATURE
<223> OTHER INFORMATION: N-terminus stearatoyl

<400> SEQUENCE: 9

Leu Ile Gly Arg
1

<210> SEQ ID NO 10
<211> LENGTH: 4
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<223> OTHER INFORMATION: N-terminus stearatoyl
<220> FEATURE:
<221> NAME/KEY: MISC_FEATURE
<223> OTHER INFORMATION: C-terminus amidation

<400> SEQUENCE: 10

Leu Ile Gly Lys
1

<210> SEQ ID NO 11
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C-terminus stearatoyl

<400> SEQUENCE: 11

Leu Ile Gly Arg
1

<210> SEQ ID NO 12
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<223> OTHER INFORMATION: C-terminus stearatoyl

<400> SEQUENCE: 12

Leu Ile Gly Arg
1

<210> SEQ ID NO 13
<211> LENGTH: 22
<212> TYPE: DNA
<213> ORGANISM: Artificial Sequence
<220> FEATURE:
<223> OTHER INFORMATION: Synthetic Primer

<400> SEQUENCE: 13
cgtcgtggac attgatggta cc                                              22

<210> SEQ ID NO 14
<211> LENGTH: 24
<212> TYPE: DNA
<213> ORGANISM: artificial sequence
<220> FEATURE:
<223> OTHER INFORMATION: Synthetic Primer

<400> SEQUENCE: 14
ggtacctcct ctcacctcct ccaa                                            24

<210> SEQ ID NO 15
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 15
accacagtcc atgccatcac                                                 20
```

```
<210> SEQ ID NO 16
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 16
tccaccaccc tgttgctgta                                             20

<210> SEQ ID NO 17
<211> LENGTH: 6
<212> TYPE: PRT
<213> ORGANISM: ARTIFICIAL SEQUENCE
<220> FEATURE:
<223> OTHER INFORMATION: SYNTHETIC PEPTIDE
<220> FEATURE:
<221> NAME/KEY: MISC_FEATURE
<223> OTHER INFORMATION: C-terminal amidation

<400> SEQUENCE: 17

Ser Leu Ile Gly Arg Leu
1               5

<210> SEQ ID NO 18
<211> LENGTH: 6
<212> TYPE: PRT
<213> ORGANISM: ARTIFICIAL SEQUENCE
<220> FEATURE:
<223> OTHER INFORMATION: SYTHETIC PEPTIDE
<220> FEATURE:
<221> NAME/KEY: MISC_FEATURE
<223> OTHER INFORMATION: C-TERMINAL AMIDATION

<400> SEQUENCE: 18

Ile Ser Ser Leu Arg Gly
1               5
```

TREATMENT OF DRY EYE

FIELD OF THE INVENTION

The present invention relates to compositions containing a peptide for therapeutic treatment of ocular conditions, including dry eye disease.

BACKGROUND OF THE INVENTION

Dry eye disease is a condition where the tear film loses water and becomes more concentrated, which can cause a corresponding rise in tear osmolarity. This increased osmolarity can result in symptoms such as a sandy-gritty feeling in the eye, burning, irritation, or a foreign-body sensation. As set forth in US Patent Application No. 2003/0203849, dry eye patients have been increasing in recent years with spread of use of contact lenses and increase in a VDT-operation.

Also as reported in US Patent Application No. 2003/0203849, lacrimal fluid serves other functions in addition to prevention of dry eye, such as, protection of cornea and conjunctiva, bacteriostatic action, prevention of infection with bacteria, fungus, virus and the like, feeding of oxygen and a variety of nutritions to cornea and removal of a carbon dioxide gas and metabolites therefrom, dilution and removal of harmful stimuli in the case where cornea and conjunctiva injured, transportation of liquid components such as epidermal growth factors which participate in wound healing and the like and hematocyte components such as fibronectin and the like to the injured portion, retainment of cornea and a conjunctival epithelial cell, regulation of wound healing.

As set forth in U.S. Patent Application No. 2005/0025810, dry eye disease may result from a number of s the following factors: (i) the disease may be a natural part of the aging process, affecting 15%-20% of adults over age 40; (ii) the disease may result from pathological processes such as diseases of the lacrimal glands, mucus glands, and/or lipid producing glands, and may occur with cell infiltration or atrophy of the lacrimal gland (Sjögren's syndrome); and (iii) estrogen deficiency in postmenopausal women may result in dry eye disease.

The proteinase-activated receptor-2 (PAR-2) is a G-protein-coupled receptor that is activated by proteolytic cleavage of the amino terminus extracellular domain, which unmasks a tethered peptide ligand that auto activates the receptor. PAR-2 is activated by trypsin and mast cell tryptase (see, e.g., Nystedt, et al., Eur J. Biochem 232(1):84-89 (1995); Bohm, et al., Biochem J 314, 1009-1016 (1996); and Molino, et al., J. Biol Chem 272(7):4043-49(1997)), as well as by synthetic peptides corresponding to the first amino acids of the receptor's tethered ligand: SLIGKV-$NH_2$ (human sequence) or SLIGRL-$NH_2$ ("SLIGRL"; mouse and rat sequence which is actually more potent than the human sequence for PAR-2 activation).

PAR-2 is expressed in many tissues, including the human cornea and human corneal epithelial cell lines (see, R Lang et al, Invest Ophthalmol Vis Sci. 44(1):99-105 (2003)). PAR-2 activity has been associated with inflammatory reactions in many tissues (see, e.g., Steinhoff et al, J Neurosci. 16;23(15):6176-80 (2003), Seeliger, et al., FASEB J. 17(13):1871-85(2003), and Uehara, et al., J Immunol 170(11):5690-96 (2003)).

PAR-2 activation in corneal epithelial cells induce intracellular calcium rise followed by pro-inflammatory cytokines release (R Lang et al, Invest Ophthalmol Vis Sci. 44(1):99-105 (2003)). PAR-2 activation by SLIGRL was shown to induce Tear Secretion in Rats (Nishikawa H et al, J Pharmacol Exp Ther. 2005 January ;312(1):324-31). US Patent Application No. 2003/0203849 discloses the use of the peptide SLIGRL, which activates PAR-2, for promoting tear secretions.

Mucin1 is one of the mucins expressed in the ocular surface (see Gibson, Exp Eye Res. 78(3)379-88 (2004)). Since ocular surface drying diseases also alter mucin production, it is expected that studies of mucin gene regulation may yield treatment modalities for these diseases (see Gibson, Exp Eye Res. 78(3)379-88 (2004)).

Applicants have unexpectedly found that the peptide LIGR induces the expression of the mucin1 gene in corneal epithelial equivalents. Applicants have found that unlike SLIGRL, the peptide LIGR does not induce calcium mobilization, and does not induce the secretion of inflammatory mediators, so the peptide is not activating PAR-2 like SLIGRL. Moreover, since LIGR is not inducing the secretion of inflammatory mediators, the peptide could be more useful in the treatment of dry eye conditions.

SUMMARY OF THE INVENTION

In one aspect, the present invention features a method to treat ocular conditions, such as dry eye, in a mammal comprising intraocularly administering a composition including a peptide of the formula $R_1$
>$A_1$-$A_2$-$A_3$-$A_4$-$R_3$
$R_2$ $A_1$ is Val, Leu, Ile, or Cha;
$A_2$ is Val, Leu, Ile, or Cha;
$A_3$ is Gly or Ala;
$A_4$ is Lys, Arg, or Har;
each $R_1$ and $R_2$, independently, is H, $C_{1-12}$ alkyl, $C_{7-10}$ phenylalkyl, or C(=O)$E_1$, where $E_1$ is $C_{1-20}$ alkyl, $C_{3-20}$ alkenyl, $C_{3-20}$ alkynyl, phenyl, 3,4-dihydroxyphenylalkyl, naphthyl, or $C_{7-10}$ phenylalkyl; provided that when either $R_1$ or $R_2$ is C(=O)$E_1$, the other must be H; and
$R_3$ is OH, $NH_2$, $C_{1-12}$ alkoxy, $C_{7-10}$ phenylalkoxy, $C_{11-20}$ naphthylalkoxy, $C_{1-12}$ alkylamino, $C_{7-10}$ phenylalkylamino, or $C_{11-20}$ naphthylalkylamino;

or a cosmetically acceptable salt thereof.

Other features and advantages of the present invention will be apparent from the detailed description of the invention and from the claims

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)).

Definitions

What is meant by "treat dry eye" is means the treatment (e.g., complete or partial alleviation or elimination of symptoms of dry eye) and/or prevention or inhibition of the symptoms of dry eye. Such treatment includes, but is not limited to, promoting lacrimal secretion.

As used herein, "intraocularly administering" means directly laying on or spreading on or around the eye, e.g., by use of the hands or an applicator such as a wipe, a contact lens, a dropper, or a spray.

As used herein, "cosmetically-acceptable" means that the peptides, other ingredients, carrier, or compositions which the term describes are suitable for use in contact on or around the eye without undue toxicity, incompatibility, instability, irritation, allergic response, and the like.

As used herein, "safe and effective amount" means an amount of the peptide or composition sufficient to treat the ocular condition, such dry eye, but low enough to avoid serious side effects. The safe and effective amount of the compound or composition will vary with the condition of the eye being treated, the age of the end user, the duration and nature of the treatment, the specific compound or composition employed, the particular cosmetically-acceptable carrier utilized, and like factors.

Peptides

The composition of the present invention comprises a peptide of the formula $R_1$
$\quad >A_1\text{-}A_2\text{-}A_3\text{-}A_4\text{-}R_3$
$R_2$ wherein:
$A_1$ is Val, Leu, Ile, or Cha;
$A_3$ is Val, Leu, Ile, or Cha;
$A_4$ is Gly or Ala;
$A_5$ is Lys, Arg, or Har;
each $R_1$ and $R_2$, independently, is H, $C_{1-12}$ alkyl, $C_{7-10}$ phenylalkyl, or $C(=O)E_1$, where $E_1$ is $C_{1-20}$ alkyl, $C_{3-20}$ alkenyl, $C_{3-20}$ alkynyl, phenyl, 3,4-dihydroxyphenylalkyl, naphthyl, or $C_{7-10}$ phenylalkyl; provided that when either $R_1$ or $R_2$ is $C(=O)E_1$, the other must be H; and
$R_3$ is OH, $NH_2$, $C_{1-12}$ alkoxy, $C_{7-10}$ phenylalkoxy, $C_{11-20}$ naphthylalkoxy, $C_{1-12}$ alkylamino, $C_{7-10}$ phenylalkylamino, or $C_{11-20}$ naphthylalkylamino;
or a cosmetically acceptable salt thereof.

In one embodiment, $R_1$ and $R_2$, which are bound to the N-terminus of the peptide, are both H. In another embodiment, $R_1$ is H and $R_2$ is $C(=O)E_1$ (e.g., palmitoyl, oleatoyl, or stearatoyl).

Examples of peptides of the present invention include, but are not limited to $H_2$-Leu-Ile-Gly-Arg-$NH_2$ (Peptide 1, SEQ ID NO:1), $H_2$-Leu-Ile-Gly-Lys-$NH_2$ (SEQ ID NO:2), $H_2$-Leu-Ile-Gly-Arg-OH (SEQ ID NO:3), $H_2$-Leu-Ile-Gly-Lys-OH (SEQ ID NO:4), Palmitoyl-Leu-Ile-Gly-Arg-$NH_2$ (SEQ ID NO:5), Palmitoyl-Leu-Ile-Gly-Lys-$NH_2$ (SEQ ID NO:6), Palmitoyl-Leu-Ile-Gly-Arg-OH (SEQ ID NO:7), Palmitoyl-Leu-Ile-Gly-Lys-OH (SEQ ID NO:8), Stearatoyl-Leu-Ile-Gly-Arg-$NH_2$ (SEQ ID NO:9), Stearatoyl-Leu-Ile-Gly-Lys-$NH_2$ (SEQ ID NO:10), Stearatoyl-Leu-Ile-Gly-Arg-OH (SEQ ID NO:11), and Stearatoyl-Leu-Ile-Gly-Lys-OH (SEQ ID NO:12), or a cosmetically-acceptable salt thereof.

The symbol $A_1$, $A_2$, or the like used herein stands for the residue of an alpha-amino acid. Such symbols represent the general structure, —NH—CH(X)—CO— or =N—CH(X)—CO— when it is at the N-terminus or —NH—CH(X)—CO— when it is not at the N-terminus, where X denotes the side chain (or identifying group) of the alpha-amino acid, e.g., X is —CH(CH$_3$)$_2$ for Val. Note that the N-terminus is at the left and the C-terminus at the right in accordance with the conventional representation of a polypeptide chain. $R_1$ and $R_2$ are both bound to the free nitrogen atom N-terminal amino acid and the $R_3$ is bound to the free carboxyl group of the C-terminal amino acid.

"Cha" herein refers to cyclohexylalanine, "2,3-diap" refers to 2,3-diaminoproprionic acid, and "Har" refers to homoarginine. Furthermore, where the amino acid residue is optically active, it is the L-form configuration that is intended unless the D-form is expressly designated. An alkyl group, if not specified, contains 1-12 carbon atoms.

The peptide of the invention can be provided in the form of cosmetically acceptable salts. Examples of preferred salts are those with therapeutically acceptable organic acids, e.g., acetic, palmitic, oleic, stearic, lactic, maleic, citric, malic, ascorbic, succinic, benzoic, salicylic, methanesulfonic, or pamoic acid, as well as polymeric acids such as tannic acid or carboxymethyl cellulose, and salts with inorganic acids such as the hydrohalic acids (e.g., hydrochloric acid), sulfuric acid or phosphoric acid.

The amount of peptide present in the composition will depend on the peptide used. The peptide typically will be present in the composition in an amount from about 0.001% to about 10% by weight, in particular in an amount from about 0.01% to about 5% by weight.

The method for synthesizing peptides of the present invention are well documented and are within the ability of a person of ordinary skill in the art. See, e.g., Bodanszky M, Int J Pept Protein Res 25(5):449-74 (1985), Fmoc Solid Phase Peptide Synthesis, eds. Chan, W. & White, P. (Oxford University Press, 2000), and Chemical Approaches to the Synthesis of Peptides and Proteins, Lloyd-Williams, P. et al. (CRC Press, 1997).

Topical Compositions

On or more of the peptides may be administered in a topical composition for treatment of dry eye. In one embodiment, the peptide is formulated for topical administration to stimulate tear production by administration of a composition containing the peptide. The composition may be applied once or more times a day.

Forms of the composition include, but are not limited to, solutions, ointments, ophthalmic inserting agents, gels, emulsions, suspensions and the like. In one embodiment, modifications such as sustained-releasing, stabilizing, or easy-absorbing properties may be further applied to such the preparations. In one embodiment, the composition is sterilized, for example, by filtration through a microorganism separating filter, heat sterilization, or the like.

In one embodiment, the peptide is contained in an aqueous-based cream excipient. In one embodiment, the cream composition is applied to the eye at bedtime, but it may be applied any time throughout the day. In another embodiment, the peptide is formulated as a solution or suspension and is applied topically in the form of eye drops.

In one embodiment, the composition contains a buffer, such as a borate buffer.

The peptide may also be administered by injection. Examples of injections include, but are not limited to, intravitreal administration (injection into the vitreous), subconjunctival injection (injection into the subconjunctiva), or retrobulbar injection (injections behind the eyeball).

For long-term delivery of the peptide, a matrix composition containing the peptide may be implanted into the eye. In one embodiment, a surgically implanted matrix composition may be a reservoir container having a diffusible wall (e.g., of polyvinyl alcohol or polyvinyl acetate) containing quantities of the peptide. In one embodiment, quantities of the peptides may be incorporated into a polymeric matrix composition made of a polymer such as polycaprolactone, poly(glycolic) acid, poly(lactic) acid, or a polyanhydride, or a lipid such as sebacic acid. Such a matrix composition may be implanted on the sclera or in the eye. In one embodiment, the matrix composition may be implanted intraocularly to result in sustained release of the peptide over a period of time.

In one embodiment, the composition contains the peptide in an alginic acid matrix between membranes which are controlled releasing membranes of an insoluble ethylene-vinyl acetate copolymer. Such a composition can placed inside eyelids.

In addition, additives such as solvents, bases, solution adjuvants, suspending agents, thickening agents, emulsifying agents, stabilizing agents, buffering agents, isotonicity adjusting agents, soothing agents, preservatives, corrigents, flavoring agents, coloring agents, excipients, binding agents, lubricants and the like can be added to a preparation, depending on the dosage forms (known dosage forms such as solutions, ointments, ophthalmic inserting agents, gels, emulsions, suspensions, solid eye drops and the like). Additionally, various additives such as pH adjusting agents, gelling agents, solubilizing agents, surfactants, absorption-promoting agents, dispersing agents, preservatives, solubilizing agents and the like can be used.

In one embodiment, the composition can be applied to an eye drop for contact lens, a washing solution for contact lens, a preserving solution for contact lens, or a contact lens composition.

When the composition of the present invention is used as the eye drop for contact lens, the washing solution for contact lens and the preserving solution for contact lens, a surfactant may be incorporated therein. Non-limiting examples of surfactants includes nonionic surfactants such as polyoxyethylene-polyoxypropylene block copolymer, polyoxyethylene/polyoxypropylene-substituted ethylenediamine, Polysorbate 80, polyoxyethylene hydrogenated castor oil, polyoxyethylenestearate and the like, amphoteric surfactants such as alkylpolyaminoethyl glycine and the like, and anionic surfactants such as alkylbenzene sulfonate, alkyl sulfate and the like and, among them, nonionic surfactants are the most preferable in light of safety to eyes. An amount of the surfactant to be incorporated may be from about 0.001 to about 5%, by weight, such as from about 0.01 to about 1%, by weight.

The eye drop for contact lens, the washing solution for contact lens and the preserving solution for contact lens having a generally used composition may be used, and the additives to be used therein may be properly selected from the additives described above for the ophthalmic preparation for topical administration. The eye drop for contact lens, the washing solution for contact lens and the preserving solution for contact lens may be produced according to the method similar to that as described above for the ophthalmic preparation for topical administration.

In one embodiment, a drug-sustained releasing contact lens may be produced in which the composition for promoting lacrimal secretion of the present invention is retained in and/or adhered to a contact lens. The contact lens may be produced using the known materials, for example materials for water-containing soft ophthalmic lens as described in U.S. Pat. No. 5,817,726, 2-hydroxyethyl methacrylate polymers as described in U.S. Pat. No. 5,905,125, ophthalmic lens materials as described in European Patent Application No. 781,777, molded ophthalmic collagen gels as described in Japanese Patent Application No. 11-197234, the hydrogel lens which is coated with a lipid layer in advance as described in U.S. Pat. No. 5,942,558. Additionally, known materials such as methacrylic acid ester polymers, copolymers of oligosiloxanylalkyl(meth) acrylate monomers/methacrylic acid ester monomer and the like may be used.

Generally used contact lens such as hard or rigid cornea-type lens, and gel, hydrogel or soft-type lens which are produced from the above known materials may be used.

The sustained-releasing contact lens may be produced, for example, by incorporating in or adhering to the contact lens the composition for promoting lacrimal fluid secretion of the present invention according to the known methods for producing the drug sustained-releasing contact lens as described in Japanese Patent Application No. 11-24010 and U.S. Pat. Nos. 5,658,592 and 6,027,745. Specifically, the drug sustained-releasing contact lens may be produced by adhering to a part of the contact lens a finely-divided or gel drug sustained-releasing agent which is prepared from a component which activate PAR-2 and polymers such as polyvinyl pyrrolidone, sodium hyaluronate and the like. In addition, the drug sustained-releasing contact lens may be produced by forming a drug reservoir such as by producing a contact lens from a member which forms a front surface of the lens and a member which forms a rear surface of the lens. Also, the contact lens of the present invention may be produced according to the known methods for producing the drug sustained-releasing contact lens other than those described above.

Additional Active Agents

In one embodiment, the topical composition further comprises other active agents in addition to the peptides for treatment of dry eye, including, but not limiting to, anti-infective agents, antibiotics, antiviral agents, anti-inflammatory drugs, antiallergic agents, vasoconstrictors, vasodilators, local anesthetics, analgesics, intraocular pressure-lowering agents, immunoregulators, anti-oxidants, vitamins and minerals, and the like Examples of anti-infective agents include, but are not limited to, silver, iodine and the like.

Examples of antibiotics include, but are not limited to, aminoglucosides, quinolones, macrolides, cephems, and sulfa drugs such as sulfamethoxazole, sulfisoxazole, sulfisomidine, sulfadiazine, sulfadimethoxine, sulfamethoxypyridazine.

Examples of antivirals include, but are not limited to, famciclovir, penciclovir, and acyclovir.

Examples of nonsteroidal anti-inflammatory drugs include, but are not limited to, indomethacin, diclofenac, pranoprofen, tiaprofenic acid, and tolfenamic acid. Examples of steroidal anti-inflammatory drugs include, but are not limited to, prednisolone. Examples of other anti-inflammatories include, but are not limited to, dipottasium glycyrrhizinate, allantoin, ϵ-aminocaproic acid, berberine chloride, berberine sulfate, sodium azulenesulfonate, zinc sulfate, zinc lactate, and lysozyme chloride.

Examples of antiallergics include, but are not limited to, ketotifen, oxatomide, cetirizine, sodium cromoglicate.

Examples of antihistamines include, but are not limited to, mequitazine, chlorpheniramine maleate, diphenhydramine hydrochloride.

Examples of vasoconstrictors include, but are not limited to, naphazoline, tetrahydrozoline, oxymethazoline, phenylephrine, ephedrines, and epinephrine.

Examples of local anesthetics include, but are not limited to, lidocaine hydrochloride, procaine hydrochloride, and dibucaine hydrochloride.

Examples of immunmodulators include, but are not limited to, cylcosporin A and tacrolimus.

Examples of vitamins include, but are not limited to, vitamin A, vitamin C, vitamin E (e.g. alpha-, beta-, gamma-, or delta-tocopherols and tocotrienols), vitamin $B_1$, $B_2$, $B_6$, and $B_{12}$. In addition, other vitamins such as nicotinates, pantothenates, biotin and the like can be used.

Examples of anti-oxidants include, but are not limited to, vitamins such as vitamin A and vitamin C.

The present invention will be further illustrated below by way of Examples, but the present invention is not limited thereto.

EXAMPLE 1

LIGR Induces the Expression of Mucin 1 (MUC1) in Corneal Epithelial Equivalents Human corneal equivalents were purchased from SkinEthic Laboratories (Nice, France). Equivalents were allowed to equilibrate in SkinEthic growth medium overnight at 5% $CO_2$, and were then treated with SLIGRL (SEQ.ID.NO.17) (200 μM), LIGR (SEQ.ID.NO.1) (200 μM) or Phosphate buffered saline (PBS) as a control. Treatment was refreshed everyday. At the end of the $6^{th}$ day, equivalent samples were harvested. Total RNA was extracted from the equivalents using RNAqueous™ kit (Ambion, Austin, Tex.) according to manufacture's instructions. RNA samples were then treated with DNA-free kit (Ambion, Austin Tex.). 25 nanograms of total RNA from each sample were amplified using OneStep RT-PCR kit (Qiagen, Valencia, Calif.) according to the manufacture's instructions. PCR Primers were synthesized by Integrated DNA Technologies (Coralville, Iowa). Primer sequences are listed in table 1. Each RT-PCR reaction contained 30 pmol of each primer of MUC1 or 10 pmol of each primer of glyceraldehyde-3-phosphate dehydrogenase (GAPDH). Each PCR cycle consisted of denaturing for 50 seconds at 94° C., annealing for 1 minutes at 58° C., elongation for 1 minute at 72° C. The PCR products were resolved by electrophoresis in 1% agarose gel and stained with ethidium bromide. Kodak Gel logic 100 imaging system was used to take gel pictures and analyze product band density.

TABLE 1

| Gene | Forward Primer | Reverse Primer | Cycle number |
|---|---|---|---|
| MUC1 | cgtcgtggacattgatggtacc (SEQ.ID.NO 13) | ggtacctcctctcacctcctccaa (SEQ.ID.NO 14) | 33 |
| GAPDH | accacagtccatgccatcac (SEQ.ID.NO 15) | tccaccaccctgttgctgta (SEQ.ID.NO 16) | 27 |

The quantified results of the RT-PCR amplification are shown in Table 2. All sample densities were normalized against GAPDH.

TABLE 2

| Treatment | Fold Change (MUC1:GAPDH) |
|---|---|
| Untreated | 1 |
| SLIGRL | 0.7 |
| LIGR | 2.1 |

These results demonstrate that LIGR, but not SLIGRL, induced the expression of the MUC1 gene.

EXAMPLE 2

SLIGRL But Not LIGR Induces Inflammatory Mediators

Human primary neonatal keratinocytes were purchased from Cascade Biologics (Portland, Oreg.). Cells were cultured in Media 154 supplemented with human keratinocytes growth supplement (Cascade Biologics) and were maintained at <80% confluency. Cells were plated at $6\times10^4$ per well in 24 well plate and allowed to attach to the well overnight with 5% $CO_2$. Cells were then treated with LIGR (50 μM), SLIGRL (50 μM), the control, scrambled peptide ISLLRG (SEQ.ID.NO.18) (50 μM) or left untreated. Each treatment was done in triplicates. 24 hours later, cell media were collected and examined for the expression and secretion of the inflammatory mediators PGE2, PGF2α, IL-8 and IL-6. $PGE_2$ and $PGF_{2\alpha}$, using ELISA kits (Cayman Chemicals, Ann Arbor, Mich.) according to manufacturer's instructions. IL-8 and IL-6 levels were detected using Beadlyte Human Multi-cytokine Detection System (Upstate Cell Signaling Solutions, Lake Placid, N.Y.) according to manufacturer's instructions. The experiment was repeated 4 times with different lots of primary keratinocytes. Data of one representative study are shown in Table 3. As shown in Table 3, SLIGRL, the known PAR-2 activator, induces 1.5-3 times increase in the expression and secretion of several inflammatory mediators. LIGR and the control, scrambled peptide did not induce these inflammatory mediators. This suggests that LIGR is acting in a manner that is different from the PAR-2 activating peptide SLIGRL, and is not associated with inflammation.

TABLE 3

| Fold change in the secretion of inflammatory mediators | | | | |
|---|---|---|---|---|
| | PGE2 | PGF2α | IL-8 | IL-6 |
| Unt. | 1 | 1 | 1 | 1 |
| SLIGRL | 2.3 | 1.5 | 3.0 | 2.7 |
| LIGR | 0.8 | 0.9 | 1.0 | 1.2 |
| ISLLRG | 0.8 | 1.0 | 1.0 | 1.1 |

EXAMPLE 3

SLIGRL But Not LIGR Induces Inflammatory Mediators In Vivo

SKH1 hairless mice, were purchased from Charles River (Kingston, N.Y.), and were housed in appropriately sized cages in an environmentally controlled room with a 12-hour light—12-hour dark photoperiod and supplied with food and water ad libitum. Mice were either untreated, or treated with LIGR or SLIGRL (From California Research Peptide Research Inc. Napa, Calif.), at 100 μM, in 70:30 ethanol: propylene glycol vehicle, once daily for 2 weeks (M-F, no treatment on weekends). Following ten days of treatment, mice were sacrificed and skin samples were processed for RNA extraction and RT-PCR. The treated skins were analyzed for the expression of Cyclooxygenase-2 (COX-2), a known inflammatory mediator. Total RNA (25 ng) from each sample was subjected to one step RT-PCR reaction using OneStep RT-PCR Kit (QIAGEN®, Valencia, Calif.) according to manufacturer's instructions. The reverse transcription was carried out for 30 minutes at 50° C. and a hot start of 15 minutes at 95° C. was then included to activate HotStar-Taq™ DNA polymerase in the reaction mix. PCR Primers were synthesized by Integrated DNA Technologies (Coralville, Iowa). Primer sequences are listed in table 4. Each RT-PCR reaction contained 30 pmol of each primer of COX-2 or 10 pmol of each primer of GAPDH. Each PCR cycle consisted of denaturing for 50 seconds at 94° C., annealing for 1 minute at 58° C., elongation for 1 minute at 72° C. The PCR products were resolved by electrophoresis in 1% agarose gel and stained with ethidium bromide. Kodak Gel logic 100 imaging system was used to take gel pictures and analyze product band density.

experiment, cells were loaded with 100 µl of Calcium Plus assay reagent component A (FLEXstation calcium Plus Assay Kit, Molecular Devices, Sunnyvale, Calif.) prepared in Hanks' Balanced Salt Solution (HBSS, Mediatech, Inc., Herndon, Va.) for 30 minutes according to the manufacturer's protocol. After loading the cells, SLIGRL, LIGR and ISSLRG (at 5× concentration in 50 µl) were added to all wells (final volume 250 µl/well), and intracellular $Ca^{2+}$ levels were subsequently assayed using the FLIPR system (Molecular Devices, Sunnyvale, Calif.) to simultaneously monitor fluorescence in all wells (Wavelength–excitation=488 nm, Wavelength–emission=510 nm) according to the manufacture's protocol. The fluorescence intensity was

TABLE 4

| Gene | Forward Primer | Reverse Primer | Cycle number |
|---|---|---|---|
| COX-2 | AGAAGGAAATGGCTGCAGAA | GCTCGGCTTCCAGTATTGAG | 33 |
| GAPDH | ACCACAGTCCATGCCATCAC | TCCACCACCCTGTTGCTGTA | 27 |

The results of this study are shown in Table 5, as expressed in the ratio of COX-2 expression to the expression of the housekeeping gene GAPDH. As shown in Table 5, COX-2 expression is increased by SLIGRL, but not by LIGR. This in vivo study further supports that LIGR is not a classic PAR-2 activator, and is not inducing pro-inflammatory mediators under physiological conditions.

captured every 3 seconds for the first 3 minutes after the addition of the peptides. The results of this study are shown in Table 6, in fluorescence units. As shown in Table 6, SLIGRL induces a dose dependent increase in intracellular calcium mobilization, using 4-40 µM peptide. However, LIGR, as well as the control, scrambled peptide, do not induce intracellular calcium mobilization even at concentrations as high as 800 µM. This example further demonstrates that LIGR is not activating PAR-2 like SLIGRL.

TABLE 5

| Treatment | COX-2:GAPDH |
|---|---|
| Untreated control | 0.353 |
| SIGRL | 1.168 |
| LIGR | 0.275 |

EXAMPLE 3

SLIGRL But Not LIGR Induces Intracellular $Ca^{2+}$ Influx

HaCaT cells were seeded in a black-wall 96-well plate at about 20,000 cells/100 µl/well and grown overnight in culture medium prior to the experiment. On the day of the

TABLE 6

| | Fluorescence intensity | | |
|---|---|---|---|
| Concentration (µM) | SLIGRL | LIGR | Scrambled peptide |
| 4 | 1386.9 | — | — |
| 8 | 1904.015 | — | — |
| 20 | 2003.095 | — | — |
| 40 | 2842.92 | 628.27 | 535.54 |
| 200 | — | 424.315 | — |
| 400 | — | — | 744.95 |
| 800 | — | 556.105 | — |

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method to treat dry eye in a mammal in need of such treatment comprising intraocularly administering to said eye a composition comprising a carrier and a peptide of the formula

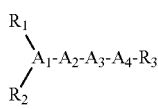

wherein:
$A_1$ is Val, Leu, Ile, or Cha;
$A_2$ is Val, Leu, Ile, or Cha;
$A_3$ is Gly or Ala;
$A_4$ is Lys, Arg, or Har;
each $R_1$ and $R_2$, independently, is H, $C_{1-12}$ alkyl, $C_{7-10}$ phenylalkyl, or $C(=O)E_1$, where $E_1$ is $C_{1-20}$ alkyl, $C_{3-20}$ alkenyl, $C_{3-20}$ alkynyl, phenyl, 3,4-dihydroxyphenylalkyl, naphthyl, or $C_{7-10}$ phenylalkyl; provided that when either $R_1$ or $R_2$ is $C(=O)E_1$, the other must be H; and
$R_3$ is OH, $NH_2$, $C_{1-12}$ alloxy, $C_{7-10}$ phenylalkoxy, $C_{11-20}$ naphthylalkoxy, $C_{1-12}$ alkylamino, $C_{7-10}$ phenylalkylamino, or $C_{11-20}$ naphthylalkylamino;

or a cosmetically acceptable salt thereof.

2. The method of claim 1, wherein $R_1$ is H, $R_2$ is H or $C(=O)E_1$ where $E_1$ is $C_{1-20}$ alkyl, and $R_3$ is OH or $NH_2$.

3. The method of claim 1, wherein $A_1$ is Leu, $A_2$ is Ile, $A_3$ is Gly, and $A_4$ is Arg or Lys.

4. The method of claim 2, wherein $A_1$ is Leu, $A_2$ is Ile, $A_3$ is Gly, and $A_4$ is Arg or Lys.

5. The method of claim 1, wherein said peptide is H2-Leu-Ile-Gly-Arg-$NH_2$ (SEQ.ID.NO: 1), $H_2$-Leu-Ile-Gly-Lys-$NH_2$ (SEQ.ID.NO: 2), $H_2$-Leu-Ile-Gly-Arg-OH (SEQ.ID.NO: 3), $H_2$-Leu-Ile-Gly-Lys-OH (SEQ.ID.NO: 4), Palmitoyl-Leu-Ile-Gly-Arg-$NH_2$ (SEQ.ID.NO: 5), Palmitoyl-Leu-Ile-Gly-Lys-$NH_2$ (SEQ.ID.NO: 6), Palmitoyl-Leu-Ile-Gly-Arg-OH (SEQ.ID.NO: 7), Palmitoyl-Leu-Ile-Gly-Lys-OH (SEQ.ID.NO: 8) Stearoyl-Leu-Ile-Gly-Arg-$NH_2$ (SEQ.ID.NO: 9), Stearoyl-Leu-Ile-Gly-Lys-$NH_2$ (SEQ.ID.NO: 10), Stearoyl-Leu-Ile-Gly-Arg-OH (SEQ.ID.NO: 11), and Stearoyl-Leu-Ile-Gly-Lys-OH (SEQ.ID.NO: 12), or a cosmetically-acceptable salt thereof.

6. The method of claim 1, wherein said peptide is $H_2$-Leu-Ile-Gly-Arg-$NH_2$ (SEQ.ID.NO: 1) or a cosmetically-acceptable salt thereof.

7. The method of claim 1, wherein said peptide is $H_2$-Leu-Ile-Gly-Arg-OH (SEQ.ID.NO: 3) or a cosmetically-acceptable salt thereof.

8. A The method of claim 1, wherein said composition is administered by topical administration.

9. A The method of claim 1, wherein said composition is administered by intraocular injection.

10. The method of claim 1, wherein said composition is administered by intraocular implantation.

11. The method of claim 3, wherein said composition is administered by topical administration.

12. The method of claim 3, wherein said composition is administered by intraocular injection.

13. The method of claim 3, wherein said composition is administered by intraocular implantation.

14. The method of claim 4, wherein said composition is administered by topical administration.

15. The method of claim 4, wherein said composition is administered by intraocular injection.

16. The method of claim 4, wherein said composition is administered by intraocular implantation.

17. The method of claim 6, wherein said composition is administered by topical administration.

18. The method of claim 6, wherein said composition is administered by intraocular injection.

19. The method of claim 6, wherein said composition is administered by intraocular implantation.

* * * * *